(12) United States Patent
Meyer

(10) Patent No.: US 10,028,774 B2
(45) Date of Patent: Jul. 24, 2018

(54) TRANSVERSE LINK HAVING SPHERICAL BALL JOINT

(71) Applicant: Alphatec Spine, Inc., Carlsbad, CA (US)

(72) Inventor: Nathan Meyer, Vista, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 322 days.

(21) Appl. No.: 15/065,364

(22) Filed: Mar. 9, 2016

(65) Prior Publication Data

US 2016/0262810 A1    Sep. 15, 2016

Related U.S. Application Data

(60) Provisional application No. 62/169,328, filed on Jun. 1, 2015, provisional application No. 62/130,377, filed on Mar. 9, 2015.

(51) Int. Cl.
*A61B 17/70*    (2006.01)

(52) U.S. Cl.
CPC ........ *A61B 17/708* (2013.01); *A61B 17/7049* (2013.01); *A61B 17/7076* (2013.01); *A61B 2017/7073* (2013.01)

(58) Field of Classification Search
CPC .............. A61B 17/7076; A61B 17/708; A61B 17/7043; A61B 17/7049
See application file for complete search history.

(56) References Cited

U.S. PATENT DOCUMENTS

| 5,397,363 | A | * | 3/1995 | Gelbard | ............. | A61B 17/7032 |
| | | | | | | 606/250 |
| 5,800,548 | A | * | 9/1998 | Martin | ............... | A61B 17/7049 |
| | | | | | | 606/250 |
| 8,506,630 | B2 | | 8/2013 | Wardlaw | | |
| 9,707,014 | B1 | * | 7/2017 | Lab | ..................... | A61B 17/7038 |
| 2012/0253402 | A1 | * | 10/2012 | McLean | ............. | A61B 17/7032 |
| | | | | | | 606/264 |
| 2014/0058450 | A1 | | 2/2014 | Arlet | | |
| 2015/0100089 | A1 | * | 4/2015 | Richelsoph | ........ | A61B 17/7001 |
| | | | | | | 606/246 |

* cited by examiner

*Primary Examiner* — Christian Sevilla
(74) *Attorney, Agent, or Firm* — Honigman Miller Schwartz and Cohn LLP

(57) ABSTRACT

A transverse link with a pair of opposing engagement members having a spherical ball bearing configured to fix a respective screw extender with respect to each other is provided. The spherical bearing is configured to allow the engagement member to rotate in three dimension so as to accommodate the position of a pair of respective screw extenders. The transverse link includes an automatic latching mechanism configured to fixed the spatial distance between the ends of the rod fixation instruments with respect to each other.

20 Claims, 8 Drawing Sheets

TRANSVERSE LINK HAVING SPHERICAL BALL JOINT

CROSS-REFERENCE TO RELATED APPLICATIONS

This application claims priority of U.S. Provisional Application Ser. No. 62/130,377 filed Mar. 9, 2015, and Ser. No. 62/169,328 filed Jun. 1, 2015, the contents of which are incorporated herein by reference.

FIELD OF THE INVENTION

A device fixing a plurality of rod fixation instruments with respect to one another is provided.

BACKGROUND

Spinal deformity is corrected by fixing the vertebrae to a rod. The rod may be shaped to have a predetermined spine curvature. Devices such as screws, implants and anchors are inserted in the vertebrae, and the vertebrae is brought up or moved towards the rod through a rod fixation instrument. Thus, the spine is set to the rod.

In operation, the rod is introduced into a slot or channel of a rod fixation instrument such as a screw extender. The screw extender is coupled to a screw which is typically fixed to a pedicle of the vertebrae. Placing the vertebrae in a proper position with respect to the rod may require the vertebrae to be moved in three dimensions so as to align slots from a plurality of screw extenders with each other, wherein the rod may be passed through each of the slots. The rod fixation lay include a rod reducer element configured to fix the vertebrae to the rod.

Manipulation of a vertebra by a single rod fixation instrument may place an undesirable load on the vertebrae. Accordingly, a transverse link is used to couple two rod fixation instruments together, creating a construct, wherein the construct may be manipulated to position the vertebrae thus spreading the load among two rod fixation instruments.

The transverse links have a base and engagement members on opposite ends of the base. The base may be configured to axially displace the engagement members from each other a predetermined distance so as to accommodate the desired position of the respective screw extender. Current engagement members provide for limited movement in three dimensional space, thus manipulation of current verse links may impose an undue load on a vertebrae as the rod fixation instruments is restricted in movement. Accordingly, it remains desirable to have a transverse link wherein the engagement members provide for greater degree of movement in all three dimensions relative to the base. It furthers desirable to have a base configured to adjust the position of the engagement members with respect to each other.

SUMMARY OF THE INVENTION

A transverse link configured to link two spaced apart rod fixation instruments, such as a screw extender, together and accommodate the rotational movement of the rod fixation instrument in three dimensions so as to distribute the load among the two rod fixation instruments is provided. The transverse link includes a base and a pair of engagement members fixedly mounted to opposing ends of the base. Each engagement member includes a receiving portion rotatably mounted to a stem. The receiving portion is configured to engage a proximal end of a screw extender so as to fix a pair of adjacent screw extenders in a fixed relationship with each other.

The distal end of each stem of respective engagement members includes a spherical ball bearing. The receiving portion includes a pair of bearing supports configured to rotatably hold the spherical ball bearing. The spherical ball bearing includes a bore, and a pair of opposing chamfered surfaces or edges extending radically about opposite ends of the bore. Each of the pair of bearing supports includes an aperture. One of the apertures is threaded. A knob having a threaded shaft is passed through the apertures of the bearing supports and the bore hole of the spherical ball bearing.

Accordingly, the spherical ball bearing may be rotatably held in between the bearing supports and is free to rotate about the axis of the threaded shaft as well as an axis orthogonal to the shaft. The chamfered edge of the spherical ball bearing increases the rotational movement of the spherical ball bearing about the axis orthogonal to the shaft relative to spherical ball bearings without the chamfered edge.

A base for use with a pair of engagement members is also provided. The base includes an elongated bore and a housing. The housing is disposed on one end of the base. Each of the engagement members includes a stem. The open ends of the bore of the base is configured to receive a corresponding stem. The base further includes an automatic latching mechanism. The automatic latching mechanism is configured to urge a blocking member against the stem so as to fix the distance between the pair of engagement members. Accordingly, overcoming the force of the biasing member releases the pair of engagement members from the fixed distance.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

FIG. 12a is a cross-sectional view of the automatic latching mechanism shown in FIG. 2, taken along lines 12a-12a.

DETAILED DESCRIPTION OF THE INVENTION

A transverse link with a pair of opposing engagement members having a spherical ball bearing configured to fix a respective screw extender with respect to each other is provided. The spherical bearing is configured to allow the engagement member to rotate in three dimension so as to facilitate the transfer of load between the pair of respective screw extenders. The screw extenders being positioned such that a respective slot is axially aligned with respect to one another so as to receive a rod. The transverse link is configured to secure two opposing rod fixation instruments together in a fixed position while simultaneously allowing the working ends of the rod fixation instruments to pivot in three dimensional space. Further, the transverse link includes an automatic latching mechanism configured to fixed the spatial distance between the ends of the rod fixation instruments with respect to each other.

Figure 1:
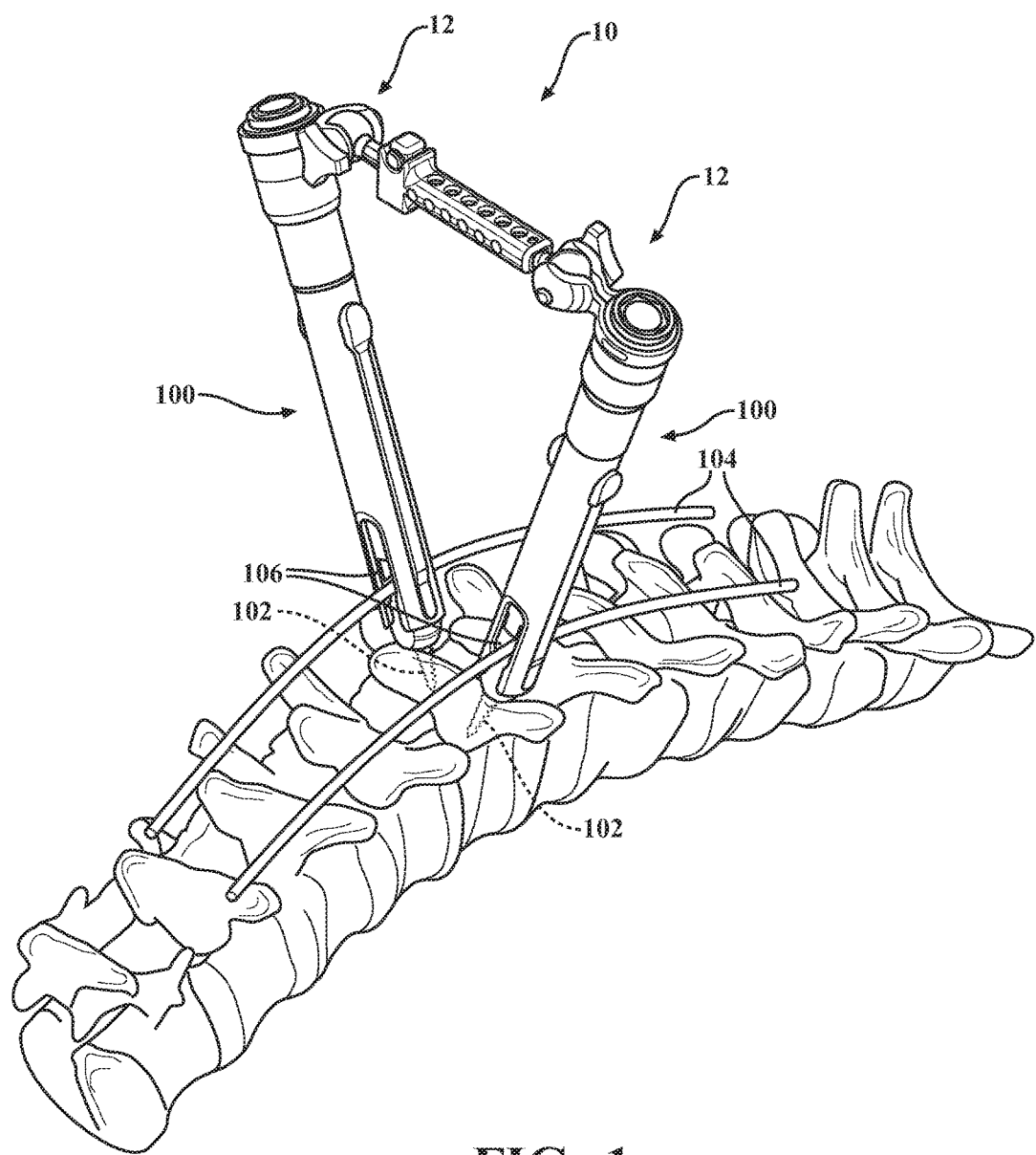
FIG. 1 is perspective view of an illustrative embodiment of the transverse link attached to opposing rod fixation instruments.

With reference first to FIG. 1, an illustration of the an illustrative embodiment of the transverse link 10 is provided. The transverse link 10 includes a pair of engagement members 12. Each engagement member 12 is mounted to opposite ends of the transverse link 10. The engagement members 12 are similar to each other, and thus a description of one is sufficient to describe the other.

FIG. 1 shows the engagement members 12 coupled to corresponding rod fixation instruments 100. For illustrative purposes, the rod fixation instruments 100 are shown as being screw extenders having a reducing function. The screw extenders 100 are coupled to respective pedicle screws 102, and a rod 104 is disposed within the slot 106 of the screw extenders 100. FIG. 1 exemplifies how the angular position of each rod fixation instrument 100 may be different from each other based upon the engagement of the rod 104 within a respective slot 106.

Figure 2:
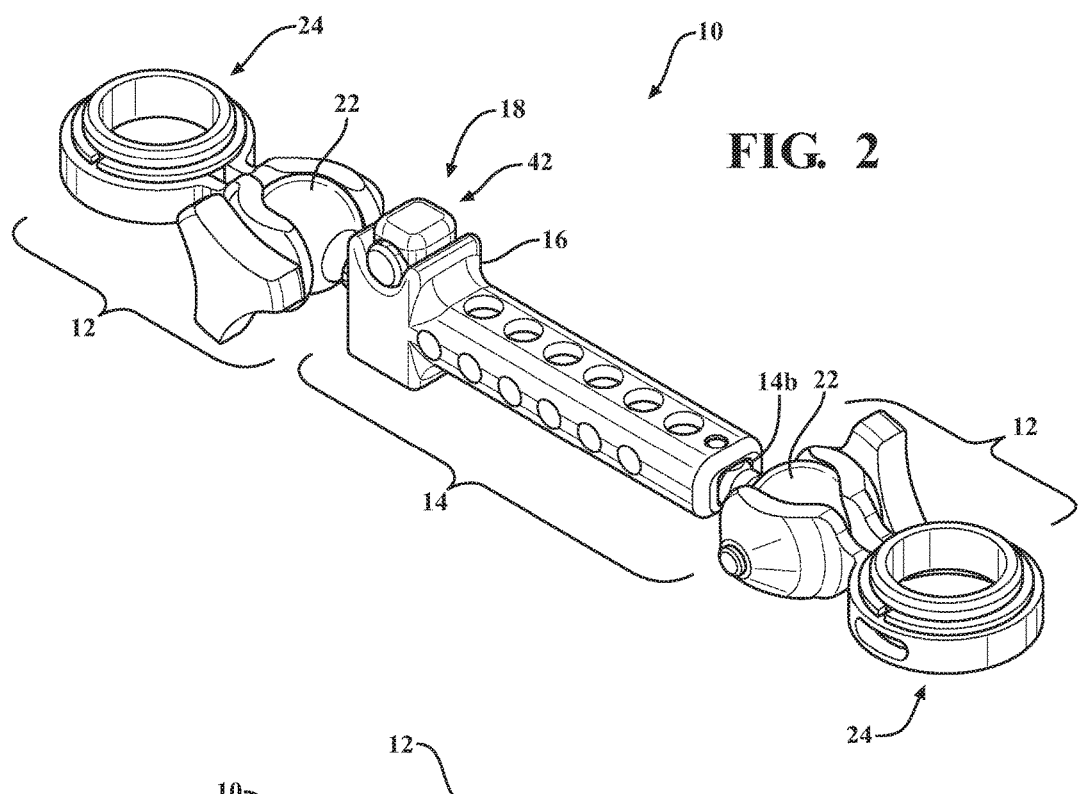
FIG. 2 is an isolated view of the transverse link shown in FIG. 1.
Figure 3:
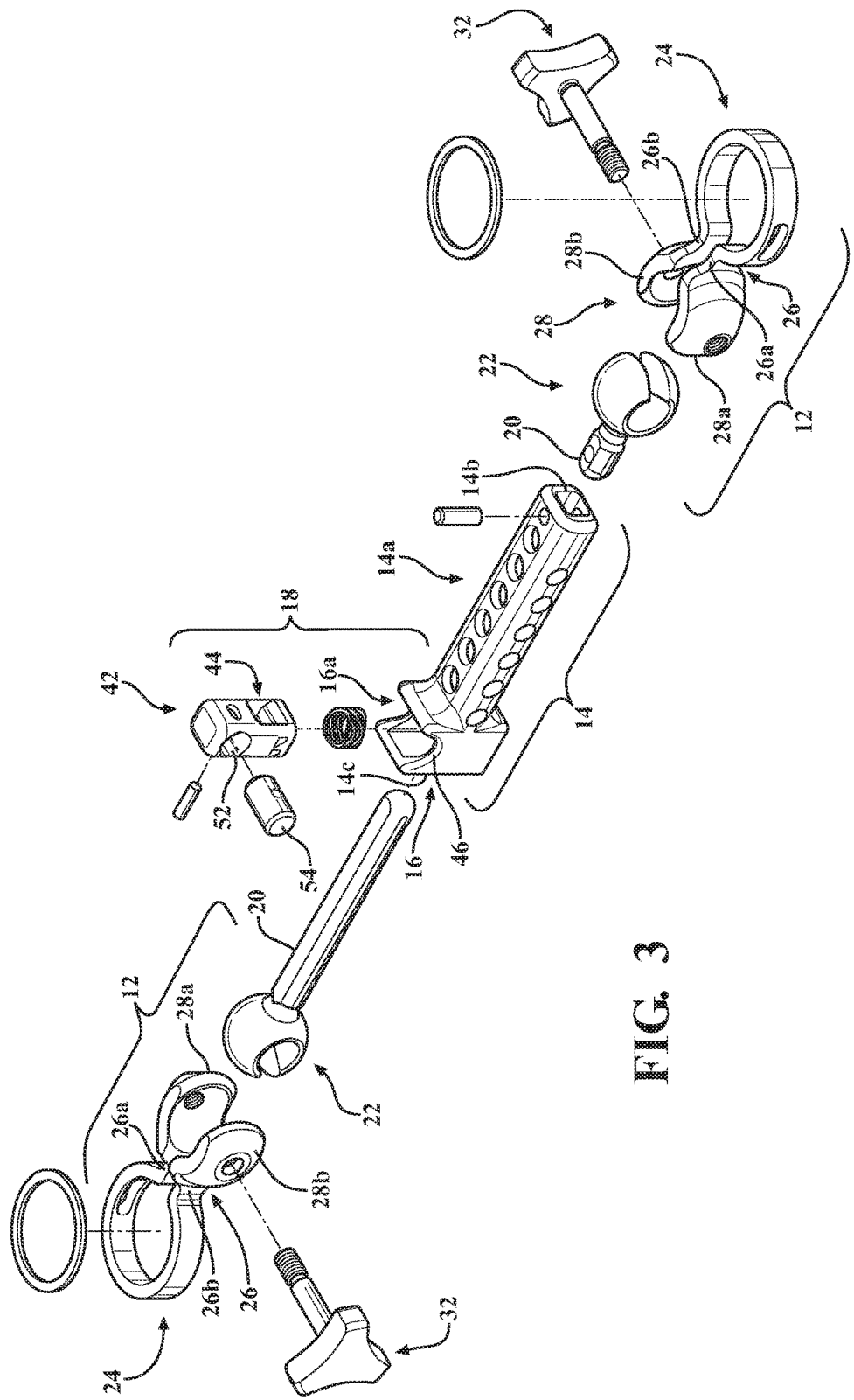
FIG. 3 is an exploded view of the transverse link shown in FIG. 2.

With now to FIGS. 2 and 3, the engagement members 12 are slidably mounted within abase 14. The base 14 includes a housing 16 and an automatic latching mechanism 18. The engagement members 12 each include a stem 20. One stem 20 is fixedly mounted to one end of the base 14 and the other stem 20 is slidably disposed within the housing 16 so as to adjust the lateral distance between the engagement members 12. The automatic latching mechanism 18 is configured to fix the distance between the engagement members 12.

The engagement members 12 further include a spherical ball bearing 22 fixedly mounted to a distal end of a respective stem 20. The engagement members further 12 include receiving portion 24 configured to engage the distal ends of the rod fixation instrument 100 (as shown in FIG. 1). The receiving portion 24 includes a neck portion 26 and bearing support 28. The bearing support includes a first bearing support 28a and a second bearing support 28b. The neck portion 26 includes a first neck 26a and a second neck 26b. The first neck 26a and the second neck 26b connect the first and second bearing supports 28a, 28b to respective ends of the receiving portion 24.

The ball bearings 22 are rotatably mounted between the bearing supports 28a, 28b of respective receiving portions 24. A tightening mechanism 32 is operatively connected to the bearing supports 28a, 28b so as to lock the spherical ball bearing 20 in a fixed relationship with the bearing supports 28a, 28b. As the bearing supports 28a, 28b are tightened, the neck portion 26 is narrowed, which in turn tightens the receiving portion onto the distal ends of respective rod fixation tools 100.

Figure 4:
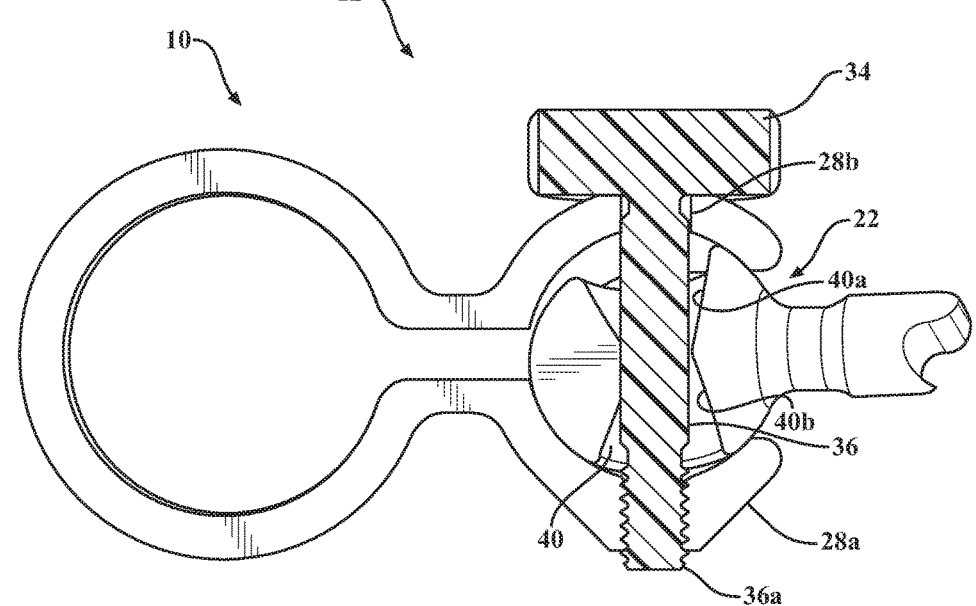
FIG. 4 is a cross-sectional view of the engagement member shown in FIG. 2 taken along lines 4-4.
Figure 11:
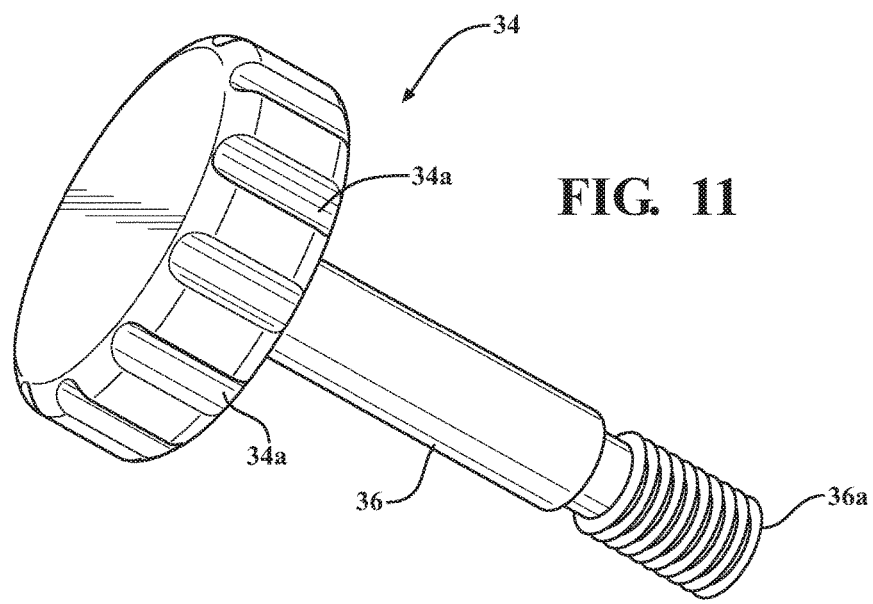
FIG. 11 is an isolated view of an embodiment of the knob.

With reference again to FIG. 2 and also to FIGS. 4 and 11, a cross-sectional view of an illustrative embodiment of the tightening mechanism 32 is provided. The tightening mechanism 32 is illustratively shown as a knob 34 mechanically coupled to the bearing supports 28. The knob 34 has a shaft 36. The distal end 36a of the shaft 36 is threaded. The knob 34 is passed through bearing support 28b and threaded to the bearing support 28a. The ball bearing 22 is rotatably held within the bearing support 28 and the knob 34 is also passed through the ball bearing 22. The tightening mechanism 32 is configured to close the bearing supports 28a and 28b against each other, so as to pinch the ball bearing 22 therebetween. It should be appreciated that the neck portion 26 narrows as indicated by the arrows shown in FIG. 4.

FIG. 11 is an isolated view of the knob 34. The knob 34 may include a plurality of indents 34a evenly spaced apart so as to help facilitate gripping the knob 34. However, it should be appreciated that the head 42 of the knob may be dimensioned to be fittingly engaged by a tool such as a wrench or a screw driver. The threaded shaft 38 is shown having a smooth portion and a threaded end. However, in instances where both apertures 28c, 28d of respective bearing supports 28a, 28b are threaded, the threaded shaft 38 may be threaded throughout the entire axial length.

Figure 5:
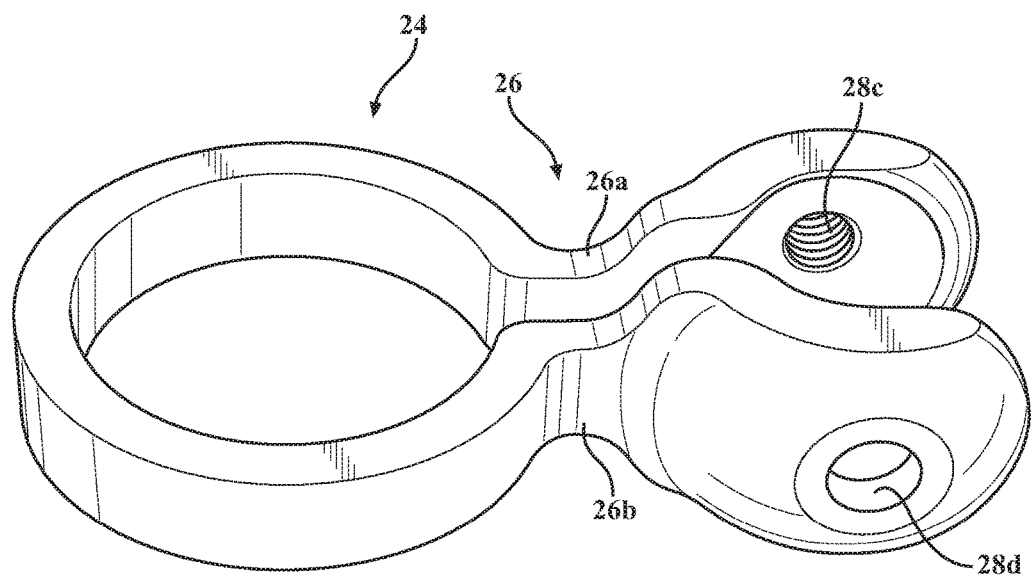
FIG. 5 is an isolated view of the receiving portion.
Figure 6:
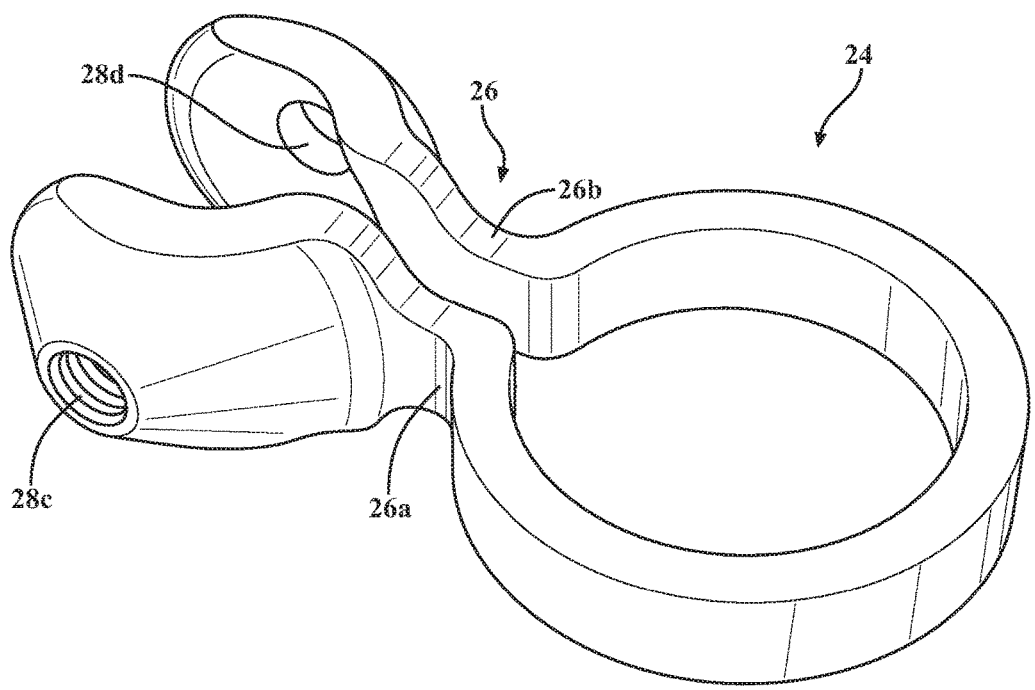
FIG. 6 is view of FIG. 5 taken from an angle.

FIGS. 5 and 6 provide an isolated view of an illustrative embodiment of the receiving portion 24, neck portion 26 and bearing support 28. The receiving portion 24 is shown generally shaped as a ring, but it should be appreciated that the shape of the receiving portion 24 may be shaped otherwise to accommodate the dimensions of a fixation instrument 100. For instance, the shape of the receiving portion 26 may be square to accommodate a fixation instrument 100 having a distal end that has a square shaped cross-section.

The first and second bearing supports 28a, 28b have a hemispherical-shaped inner surface that are configured and dimensioned to engage opposite surfaces of the spherical ball bearing 22. The first and second bearing supports 28a, 28b each includes an aperture 28c, 28d. Apertures 28c, 28d are axially aligned with each other. One of the apertures 28c is threaded.

Figure 7:
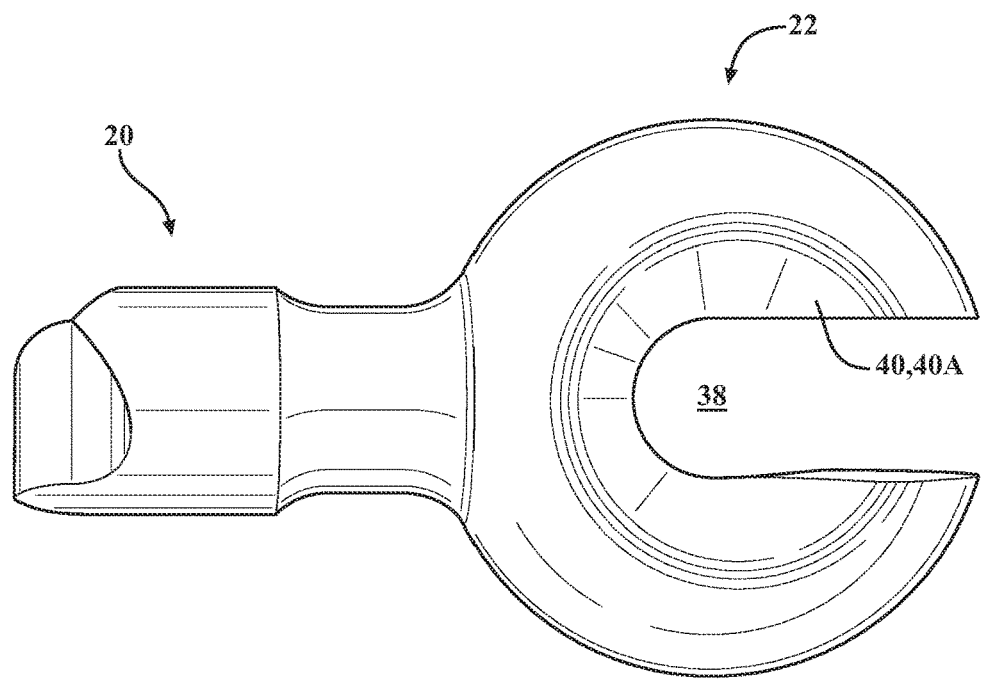
FIG. 7 is a top down view of the spherical ball bearing.
Figure 8:
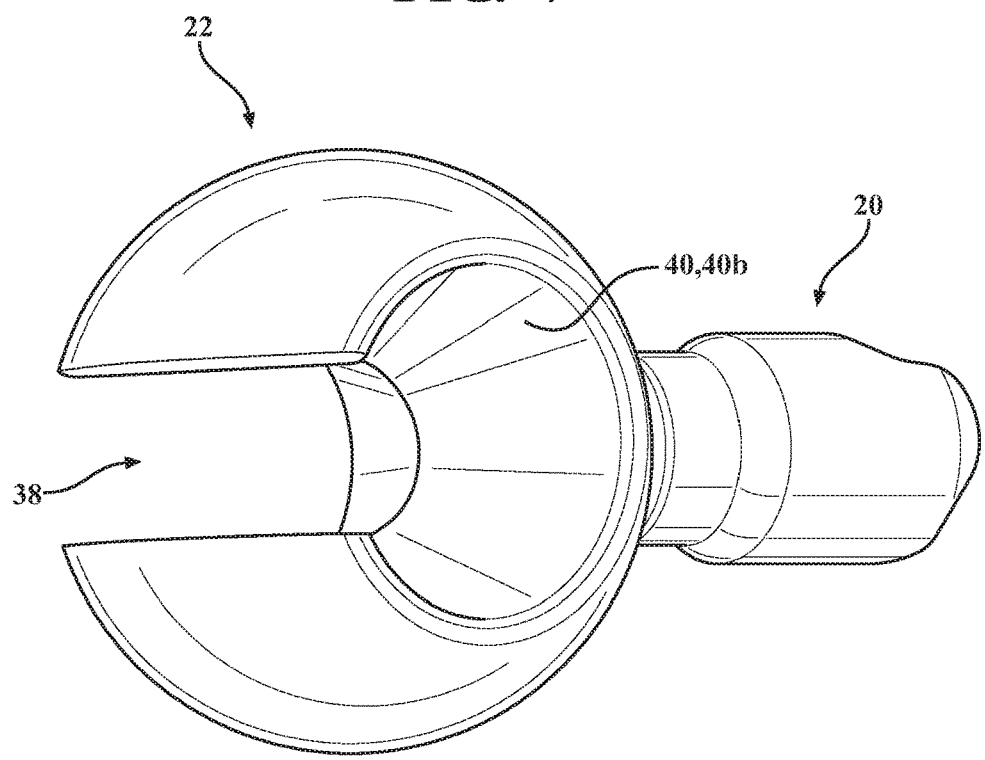
FIG. 8 is a view of FIG. 7 taken from an angle.

FIGS. 7 and 8 are an isolated view of the spherical ball bearing 22. The spherical ball bearing 22 further includes a stem 20. The stem 20 is fixed to the spherical ball bearing 22. The spherical ball bearing 20 includes a bore 38. A pair of chamfered edges 40 (the chamfered edges are generally referenced as 40, and specifically referenced herein as 40a, 40b) are formed on the top and bottom surfaces ball bearing 22 so as to form a cone. The chamfered edges 40a and 40b are disposed opposite of each other. The chamfered edges 40 also extend radially from the bore 38 and angled with respect to the axial length of the stein 20. The bore 38 is generally coaxial to the stem 20 so as to form an opening and provide the spherical ball bearing 22 with a generally C-shaped cross-section. The stem 20 is narrowed adjacent the spherical ball bearing 22 so as to accommodate the rotation of the bearing support 28 about the ball bearing 22.

The chamfered edges 40 provide clearance to allow the spherical bearing 20 greater rotation about the threaded shaft 38. The chamfered edges 34 may be disposed at an angle between 15 to 65 degrees with respect to the axis of the threaded shaft 38 so as to allow pivoting in either direction about the threaded shaft 38. The spherical bearing 20 also has up to 360 degrees of rotation about the axis of the threaded shaft 38. Turning the knob 34 in a tightening direction will lock the spherical ball bearing 20 in any of position within the bearing support 18, otherwise, the ball bearing 22 may freely swing, twist, or tilt between first and second bearing supports 28a, 28b the while loose.

FIG. 7 is atop down view of the stem 20 and the spherical ball bearing 22. FIG. 8 is a perspective view of FIG. 7 taken from the opposite side and provided to illustrate the dimensions of the chamfered edge 40. Taken as a whole, it should be appreciated that the chamfered edges 40 are similar to each other in dimension. The bore 38 is open to an edge of the spherical ball bearing 22 thus facilitating the assembly of the spherical ball bearing 22 to the bearing support 28. For example, in instances where the receiving portion 14 is assembled with the threaded shaft 36 of the knob 34 mounted to the bearing support 18, the user can simply the spherical ball bearing 22 onto the threaded shaft 38 via the slot 40. The knob 34 is then rotated within the bearing support 30 so as to clamp the spherical ball bearing 22 in a desired orientation.

Figure 9:
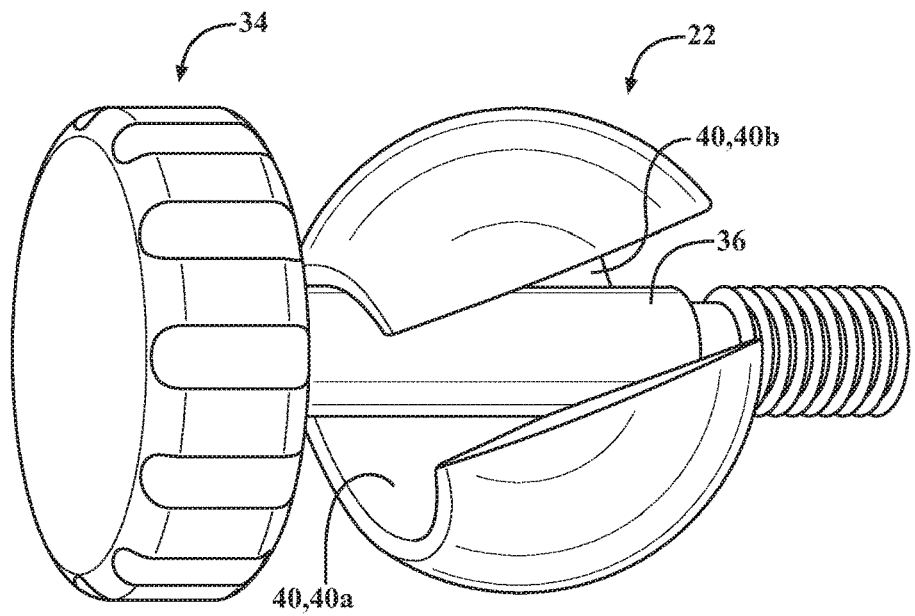
FIG. 9 is a perspective view of the knob and spherical ball bearing.
Figure 10:
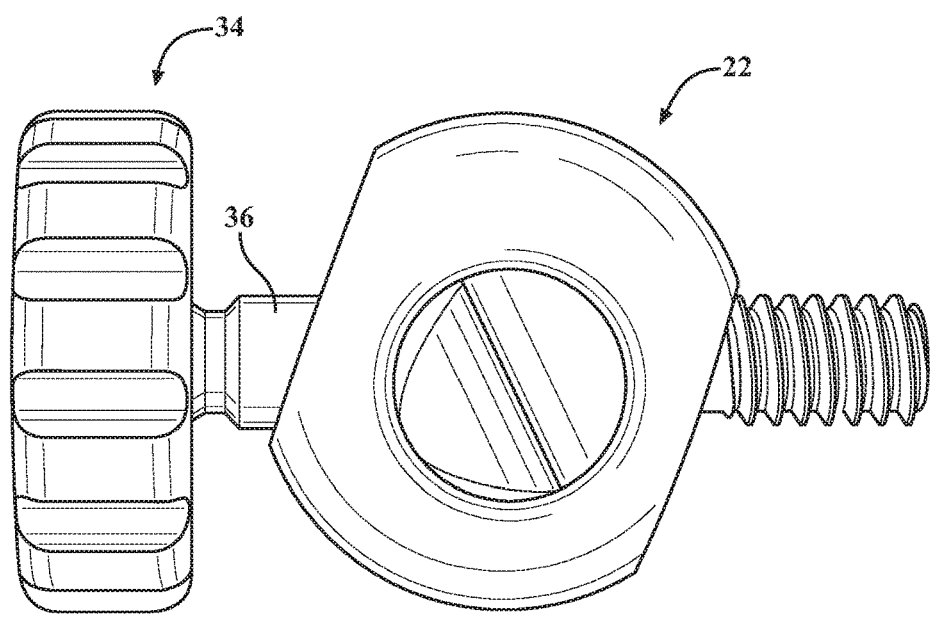
FIG. 10 is a view of FIG. 9 taken from the opposite side of the spherical ball bearing.

FIGS. 9 and 10 are an illustration of the engagement member 12 with the receiving portion 24 removed. FIGS. 9 and 10 further illustrate the degree of freedom which the chamfered edge 40 provides. Specifically, it should be appreciated that the spherical ball bearing 22 may be rotated or pivoted about the length of the threaded shaft 36 until one of the chamfered edges 40a, 40b abuts against the threaded shaft 38. Further, the spherical ball bearing 20 may be rotated about the threaded shaft 38 360 degrees.

FIGS. 9 and 10 are isolated views of the receiving portion 14 and the bearing support 18. The receiving portion 14 is shown as a collar having an open end, i.e. having a ring shape. FIGS. 9 and 10 further illustrate the hemispherical shape of the bearing support 28. Namely, the inner surface of both the first and second bearing supports 28a, 28b are dimensioned to rotatably hold the spherical ball bearing 20.

Figure 12A:
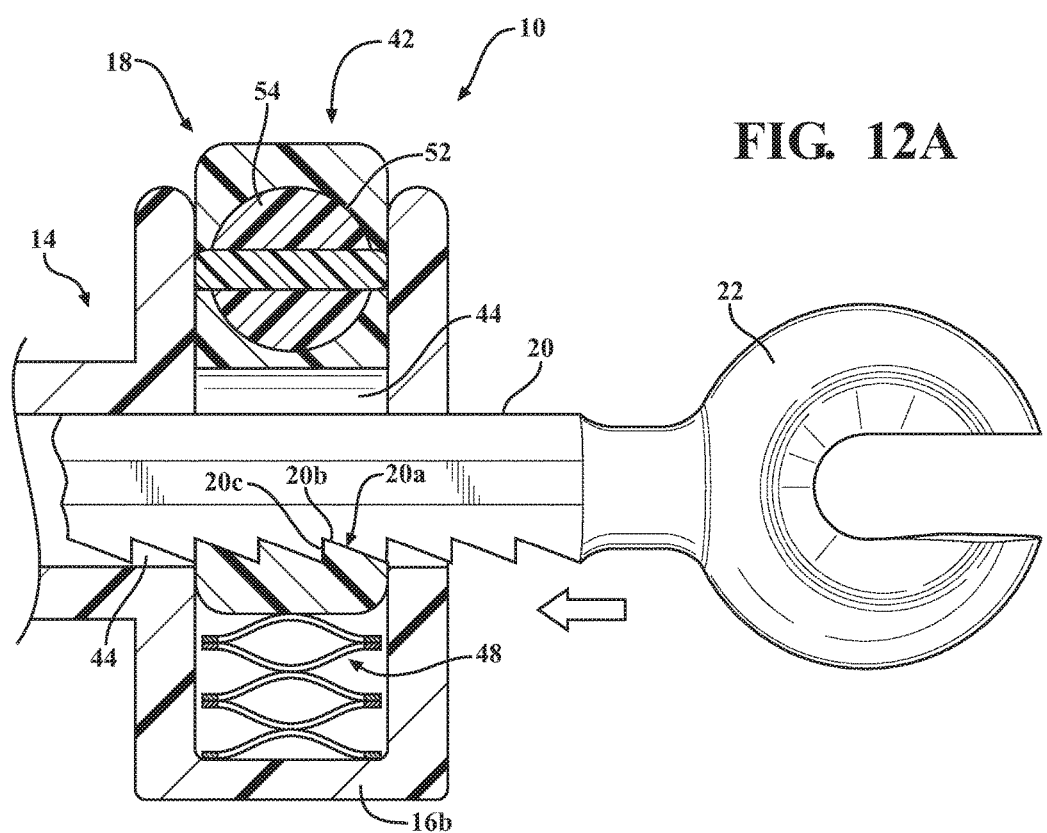
Figure 12B:
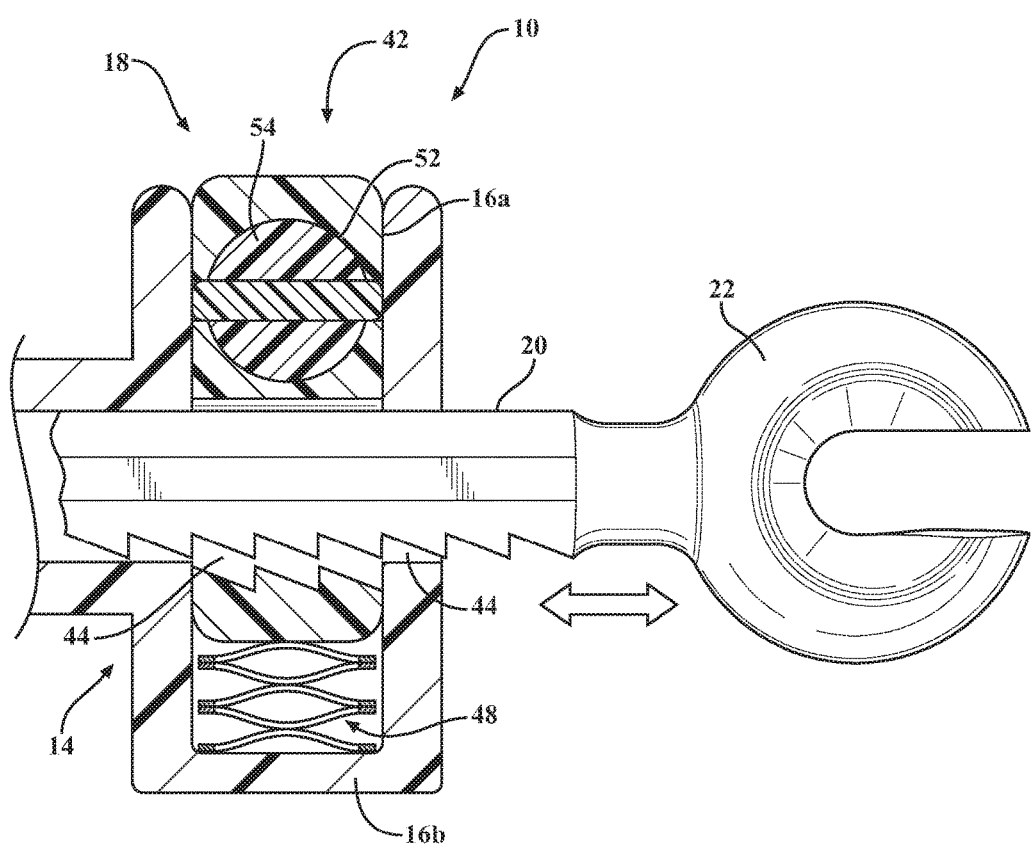
FIG. 12b is a view of FIG. 12a showing the biasing member being depressed.

With reference again to FIGS. 2 and 3 and also to FIGS. 12a and 12b, an illustrative example of a transverse link 10 is shown. The transverse link 10 includes a base 14. The base 14 includes openings 14a at each end so as to receive the proximal end of respective stems 20. The base 14 includes an automatic latching mechanism 18 configured to fix the distance between opposing engagement embers 12.

An illustrative embodiment of an automatic latching mechanism 18 includes a block member 42 having a pass-through slot 44 configured to receive an end of the stem 20. The stem 20 includes a spherical ball bearing 20 integrally formed to one end of the stem 20. A bottom surface of the stem 20 includes a plurality of teeth 20a. The teeth 20a include an angled back wall 20b opposite a generally planar front wall 20c so as to form a generally sinusoidal profile.

The base 14 is shown housing the pair of engagement hers 12. The base 14 is illustratively shown as a rectangular prism having an elongated channel 14a with open ends 14b, 14c configured to receive respective stems 20 of the engagement members 12. The base 14 includes a plurality of through holes transverse to the axis of the elongated channel 14a.

The automatic latching mechanism 18 works in concert with the housing 16. The housing 16 is formed on one end of the base 14. The housing 16 includes a central opening 16a and a bottom wall 16b. The central opening 16a is configured to receive the block member 42. The block member 42 is a generally cylindrical body having a pass-through slot 44 configured to receive the stem 20. The block member 42 sits within the central opening 16a of the housing 16 and is held therein by the disposition of the stem 20 within the pass-through slot 44.

The biasing member 48 is disposed between the bottom surface of the block member 42 and the inner surface of the housing 16. The biasing member 48 is illustratively shown as a plurality of leaf springs, but it should be appreciated that the biasing member may be a helical spring or the like. A bottom wall surface of the pass-through slot 44 includes a plurality of raised edges 50 forming a surface complimentary to the teeth 20a of the stem 20.

The block member 42 further includes a second through-hole 52 elevated above the pass-through slot 44 and generally orthogonal to the axis of pass-through slot 44. The second through-hole 52 is configured to receive a cylindrical block 54 which may be fixed to the block member 42 by a set pin. The cylindrical block 54 projects beyond the outer surface of the block member 42 and is configured to stop the block member 42 from advancing by the saddle 46 formed on the top surface of the block member 42. A biasing member 48 is also disposed within the central opening 16a between the bottom wall 16b and the block member 42 so as to urge the block member 42 away from the bottom wall 50b.

With reference again to FIGS. 12a and 12b an illustration of the operation of the latching mechanism 18 is provided. The stem 20 is disposed within the housing 16 with the teeth 20a facing the raised edges 50 of the block member 42. The user simply positions the stem 46 within the base 12 and housing 16 to the desired location, wherein the angled back walls 20b of the teeth 20a slide in and out of the depressions formed by the raised edges 50. The teeth 20a and the raised edges 50 are locked together by the constant urging force of the biasing member 48.

The teeth 20a are oriented so as to allow the angled back wall 20b to slide against the raised edges 50 as the stem 20 is pushed further into the base 14. However, the raised edges 50 lock against the planar front wall 20c of the teeth 20a so as to prevent the stem 20 from being push out of the base 14. Thus, it should be appreciated that the stem 20 is fixed within the housing 16 once the engagement members 12 are spaced apart the desired distance from each other. Accordingly, the automatic latching mechanism 18 automatically fixes the stem 46 to the housing 16.

If a user wishes to release the stem 20 from the housing sing 16. The user simply presses down on the block member 42 which overcomes the force of the biasing member 48 and displaces the raised edges 50 of the block member 42 away from the teeth 20a of the stem 20, allowing the stun 20 to be slid in and out of the housing 16.

With reference again to FIGS. 2 and 3, one of the stems 20 is fixedly mounted to one end of the base 14. The stem 20 is shorter than the other and fixed to the base 14 by a pin. Thus, establishing the distance between the pair of engagement members 12 simply requires positioning one stem 120 within the housing 16.

In operation, the user may set the positions the rod fixation instruments 100 within the body. One of the engagement members 12 is mounted to the distal end of the rod fixation instrument 100 and the other of the engagement members 12 is mounted to the distal end of the other rod fixation instrument 100. The tightening mechanism is actuated so as to secure the respective ball bearings 30 in place. Thus, as the ball bearings 30 have a chamfered edge 40, a greater degree of rotational freedom of the rod fixation instruments 100 with respect to each other is provided relative to current transverse links. The distance between the engagement members 12 may be fixed by positioning the stem 20 disposed within the housing 16. As the desired position of the engagement members 12 are achieved, the automatic latching mechanism fixes the stem 20 in place with respect to the housing 16.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

I claim:

1. An engagement member for use in a transverse link, the transverse link having a base and an axial displacement mechanism, the engagement member comprising:
   a stem having a spherical ball bearing disposed on a distal end of the stem, a proximal end of the stem capable of being disposed within the base of the transverse link, the axial displacement mechanism capable of being operatively attached to the stem so as to move the stem along an axis in and out of the base, the spherical ball bearing having a bore, and a pair of chamfered edges disposed on opposite ends of the bore, the chamfered edges extending radially about an axis of the bore;
   a receiving portion rotatably mounted to the spherical ball bearing, the receiving portion having a pair of spaced apart bearing supports configured to engage opposing surfaces of the spherical ball bearing so as to rotatably hold the spherical ball bearing therebetween; and
   a tightening member operatively connected to the bearing supports so as to lock the spherical ball bearing in a fixed relationship with the bearing supports, the tightening member having a shaft disposed within the bore, a rotational movement of the spherical bearing limited by abutment of the shaft against respective chamfered edges of the spherical ball bearing.

2. The engagement member as set forth in claim 1, wherein the tightening member is a knob, the shaft extending from the knob.

3. The engagement member as set forth in claim 2, wherein each of the pair of bearing supports includes an aperture, each of the apertures is axially aligned with the other, and one of the apertures is threaded.

4. The engagement member as set forth in claim 2, wherein at least one of the chamfered edges is angled between 15 to 65 degrees with respect to an axis of the shaft.

5. The engagement member as set forth in claim 1, wherein the stem includes a plurality of teeth.

6. The engagement member as set forth in claim 1, wherein the receiving portion is generally ring shaped.

7. The engagement member as set forth in claim 2, wherein the knob includes a plurality of indents.

8. The engagement member as set forth in claim 1, wherein the stem is narrowed adjacent the spherical ball bearing.

9. A transverse link for securing two opposing rod fixation instruments together in a fixed position while simultaneously allowing working ends of the rod fixation instruments to pivot in three dimensional space, the transverse link comprising:
   a base having an elongated bore and a housing disposed on one end of the base, the elongated bore defining a pair of open ends,
   a pair of engagement members, each of the pair of engagement members having:
      a spherical ball bearing and a stem fixedly mounted to the spherical ball bearing, the spherical ball bearing having a bore and a pair of chamfered edges disposed on opposite ends of the bore, the chamfered edges extending radially about an axis of the bore;
      a receiving portion rotatably mounted to the spherical ball bearing, the receiving portion having a pair of spaced apart bearing supports configured to engage opposing surfaces of the spherical ball bearing so as to rotatably hold the spherical ball bearing therebetween; and
      a tightening member operatively connected to the bearing supports so as to lock the spherical ball bearing in a fixed relationship with the bearing supports, the tightening member having a shaft disposed within the bore, a rotational movement of the spherical bearing limited by the abutment of the shaft against respective chamfered edges of the spherical ball bearing;
   wherein one of the stems is fixed to one end of the base and the other stem is slidably disposed within the housing; and
   an automatic latching mechanism mechanically coupled to the housing, the automatic latching mechanism configured to automatically fix at least one of the stems within the housing.

10. The transverse link as set forth in claim 9, wherein the automatic latching mechanism includes a blocking member having a pass-through slot configured to engage at least one of the stems, the blocking member disposed within a central opening of the housing, and a biasing member configured to urge the blocking member into engagement with at least one of the stems so as to fix at least one of the stems in position with respect to the housing.

11. The transverse link as set forth in claim 10, wherein at least one of the stems includes a plurality of teeth and a bottom wall surface of the pass-through slot includes a plurality of raised edges forming a surface complimentary to the teeth.

12. The transverse link as set forth in claim 10, wherein the blocking member includes a cylindrical block projecting beyond an outer surface of the blocking member, and a top surface of the housing is a saddle configured to prevent the cylindrical block from advancing.

13. The transverse link as set forth in claim 10, wherein one of the pair of stems is shorter than the other.

14. The transverse link as set forth in claim 9, wherein for at least one of the engagement members, the tightening member is a knob, the shaft extending from the knob.

15. The transverse link as set forth in claim 14, wherein, for at least one of the engagement members, each of the pair of bearing supports includes an aperture, each of the apertures is axially aligned with the other, and one of the apertures is threaded.

16. The transverse link as set forth in claim 14, wherein, for at least one of the engagement members, at least one of the chamfered edges is angled between 15 to 65 degrees with respect to an axis of the shaft.

17. The transverse link as set forth in claim 9, wherein at least one of the receiving portions is generally ring shaped.

18. The transverse link as set forth in claim 14, wherein the knob includes a plurality of indents.

19. The transverse link as set forth in claim 9, wherein, for at least one of the engagement members, the stem is narrowed adjacent the spherical ball bearing.

20. The transverse link as set forth in claim 9, wherein the base has a rectangular prism shape.

* * * * *